(12) United States Patent
Rennaker et al.

(10) Patent No.: US 10,758,121 B2
(45) Date of Patent: Sep. 1, 2020

(54) SYSTEM FOR TRAUMATIC BRAIN INJURY DETECTION USING OCULOMOTOR TESTS

(71) Applicants: Board of Regents, The University of Texas System, Austin, TX (US); University of Iowa Research Foundation, Iowa City, IA (US)

(72) Inventors: Robert Rennaker, Sachse, TX (US); Elliot Frohman, Dallas, TX (US); Randy Kardon, Iowa City, IA (US)

(73) Assignees: Board of Regents, The University of Texas System, Austin, TX (US); University of Iowa Research Foundation, Iowa City, IA (US)

( * ) Notice: Subject to any disclaimer, the term of this patent is extended or adjusted under 35 U.S.C. 154(b) by 0 days.

(21) Appl. No.: 14/633,688

(22) Filed: Feb. 27, 2015

(65) Prior Publication Data

US 2015/0245766 A1    Sep. 3, 2015

Related U.S. Application Data

(60) Provisional application No. 61/946,361, filed on Feb. 28, 2014.

(51) Int. Cl.
| | |
|---|---|
| *A61B 3/00* | (2006.01) |
| *A61B 3/11* | (2006.01) |
| *A61B 3/113* | (2006.01) |
| *A61B 3/14* | (2006.01) |
| *A61B 5/00* | (2006.01) |
| *A61B 5/03* | (2006.01) |

(52) U.S. Cl.
CPC ............ *A61B 3/112* (2013.01); *A61B 3/0025* (2013.01); *A61B 3/0041* (2013.01); *A61B 3/0075* (2013.01); *A61B 3/113* (2013.01); *A61B 3/14* (2013.01); *A61B 5/031* (2013.01); *A61B 5/4064* (2013.01)

(58) Field of Classification Search
CPC ............................ A61B 3/0075; A61B 3/0041
USPC ........................................ 351/209, 210, 246
See application file for complete search history.

(56) References Cited

U.S. PATENT DOCUMENTS

| | | | |
|---|---|---|---|
| 4,618,230 | A | 10/1986 | Ens et al. |
| 5,070,883 | A | 12/1991 | Kasahara |
| (Continued) | | | |

FOREIGN PATENT DOCUMENTS

| | | |
|---|---|---|
| EP | 2 654 030 | 10/2013 |
| WO | WO 2013/023056 | 2/2013 |

OTHER PUBLICATIONS

Fixed, Dilated Pupils Following Traumatic Brain Injury: Historical Perspectives, Causes and Ophthalmological Sequelae, Helmy et al., Acta Neurochirurgica Supplementum, vol. 114, p. 295.*

(Continued)

*Primary Examiner* — Travis S Fissel
(74) *Attorney, Agent, or Firm* — LaBatt, LLC

(57) ABSTRACT

Embodiments of the present invention comprises apparatuses and methods of measuring levels of neurological impairment. Certain embodiments of the invention comprise a headset that emits light into the user's eyes and the system tracks the pupils' orientation, movement, contraction and dilation. In specific embodiments, the headset can run a battery of tests and calculate a score indicating the user's level of neurological impairment.

20 Claims, 9 Drawing Sheets

(56) References Cited

U.S. PATENT DOCUMENTS

| | | | |
|---|---|---|---|
| 5,422,690 A | 6/1995 | Rothberg et al. | |
| 5,583,795 A * | 12/1996 | Smyth | A61B 3/0025 |
| | | | 359/630 |
| 6,260,968 B1 | 7/2001 | Stark et al. | |
| 6,702,757 B2 * | 3/2004 | Fukushima | A61B 3/112 |
| | | | 600/558 |
| 6,820,979 B1 * | 11/2004 | Stark | A61B 3/112 |
| | | | 351/206 |
| 7,854,511 B2 * | 12/2010 | Molnar | A61B 3/12 |
| | | | 351/218 |
| 7,988,287 B1 | 8/2011 | Butler et al. | |
| 8,210,680 B2 * | 7/2012 | Tanguay, Jr. | A61B 3/12 |
| | | | 351/205 |
| 8,585,609 B2 | 11/2013 | Kiderman et al. | |
| 2002/0024633 A1 * | 2/2002 | Kim | G06T 7/0012 |
| | | | 351/206 |
| 2004/0100692 A1 * | 5/2004 | Hou | G03B 21/60 |
| | | | 359/452 |
| 2005/0099601 A1 | 5/2005 | MacDougall et al. | |
| 2007/0121066 A1 * | 5/2007 | Nashner | A61B 3/0091 |
| | | | 351/210 |
| 2009/0018419 A1 | 1/2009 | Torch | |
| 2009/0213329 A1 * | 8/2009 | Kandel | A61B 3/145 |
| | | | 351/206 |
| 2010/0214532 A1 * | 8/2010 | Siminou | A61B 3/112 |
| | | | 351/206 |
| 2011/0176106 A1 | 7/2011 | Lewkowski | |
| 2011/0184320 A1 | 7/2011 | Shipps | |
| 2012/0008091 A1 | 1/2012 | Stewart | |
| 2013/0114850 A1 * | 5/2013 | Publicover | G06K 9/00604 |
| | | | 382/103 |
| 2013/0176534 A1 * | 7/2013 | Frankfort | A61B 3/113 |
| | | | 351/209 |
| 2013/0278899 A1 * | 10/2013 | Waldorf | A61B 3/0091 |
| | | | 351/209 |
| 2013/0308099 A1 * | 11/2013 | Stack | A61B 5/162 |
| | | | 351/209 |
| 2014/0039355 A1 | 2/2014 | Crisco | |
| 2014/0046193 A1 | 2/2014 | Stack | |
| 2014/0186806 A1 * | 7/2014 | Hallowell | A61B 3/112 |
| | | | 434/167 |

OTHER PUBLICATIONS

Detecting Pupillary Dilation Lag, Patricia Johnston McNussen, MD, Urbana, Illinois http://content.lib.utah.edu/utils/getfile/collection/ehsl-nam/id/3903/filename/3830.pdf.*

Effects of Spectral Characteristics of Ganzfeld Stimuli on the Photopic Negative Response (PhNR) of the ERG, Nalini V. Rangaswamy, Suguru Shirato, Muneyoshi Kaneko, Beth I. Digby, John G.Robson, and Laura J. Frishman. Invest Ophthalmol Vis Sci. Oct. 2007 ; 48(10): 4818-4828.*

Grozdanic et al., Invest Ophthalmol Vis Sci. Nov. 2007;48(11):5178-83.*

Rashbass, J. Phy&io. (1961),159,pp. 326-338.*

Assessment of optic neuropathy as a result of direct and indirect injury using non-invasive functional and structural analytical tools, Kabhilan Mohan University of Iowa, 2012.*

STIC search report, Oct. 11, 2017.*

Test—Retest Repeatability of the Pupil Light Response to Blue and Red Light Stimuli in Normal Human Eyes Using a Novel Pupillometer, Frontiers Neurology; Herbst et al. (Year: 2012).*

Broadway, David C. "How to test for a relative afferent pupillary defect (RAPD)." Community eye health vol. 25,79-80 (2012): 58-9 (Year: 2012).*

International Search Report and Written Opinion issued in International Application No. PCT/US2015/018051, dated Jun. 2, 2015.

Al-Qurainy, "Convergence insufficiency and failure of accomodation following midfacial trauma," British Journal of Oral and Maxillofacial Surgery, 1995, 5 pages.

Berne, S., "Visual Therapy for the Traumatic Brain-Injured," 1990, 4 pages.

Brahm, K., et al., "Visual Impairment and Dysfunction in Combat-Injured Servicemembers with Traumatic Brain Injury," 2009, 9 pages.

Candler, M., "Some Observations on Orthoptic Treatment Following Head Injury," The British Orthoptic Journal, 1944, 7 pages.

Capo-Aponte, J., et al., "Visual Dysfunctions and Symptoms During the Subacute Stage of Blast-Induced Mild Traumatic Brain Injury," Military Medicine, 2012, 11 pages.

Chen, J., et al., "Pupillary reactivity as an early indicator of increased intracranial pressure: The introduction of the Neurolofical Pupil Index," Surgical Neurology International, 2011, 12 pages.

Ciuffreda, K., et al., "Oculomotor Rehabilitation in Traumatic Brain-Injured Patients," Journal of Behavioral Optometry, 1996, 8 pages.

Ciuffreda, K., et al., "Occurrence of oculomotor dysfunctions in acquired brain injury: A retrospective analysis," Optometry, 2007, 7 pages.

Ciuffreda, K., et al., "Vision therapy for oculomotor dysfunctions in acquired brain injury: A retrospective analysis," Optometry, 2008, 5 pages.

Cohen, A., "A Case in Point: Rehabilitation a Stroke Patient," Journal of the American Optometric Association, 1978, 4 pages.

Cohen, A., et al. "Optometric approach to the rehabilitation of the stroke patient," Northport VA Medical Center, 1981, 8 pages.

Cohen, M., et al. "Convergence insufficiency in brain-injured patients," Brain Injury, 1989, 6 pages.

Cohen, A., "Optometric management of binocular dysfuctions secondary to head trauma: case reports," Journal of the American Optometric Association, 1992, 8 pages.

Dashnaw, M., et al., "An overview of the basic science of concussion and subconcussion: where we are and where we are going," Neurosurg Focus, 2012, 9 pages.

Gamlin, P., "Neural Mechanisms for the Control of Vergence Eye Movements," Vision Science Research Center, University of Alabama at Birmingham, 2002, 9 pages.

Gianutsos, R., et al., "Rehabilitative Optometric Services for Survivors of Acquired Brain Injury," Optometric Services in Brain Injury, 1998, 6 pages.

Goodrich, G., et al., "Visual function in patients of a polytrauma rehabilitation center: A descriptive study," Journal of Rehabilitation Research & Development, 2007, 9 pages.

Goodrich, G., et al., "Mechanisms of TBI and Visual Consequences in Military and Veteran Populations," American Academy of Optometry, 2013, 8 pages.

Gould, T., et al., "Altered Performance on an Ocular Fixation Task in Attention-Deficit/Hyperactivity Disorder," Society of Biological Psychiatry, 2001, 3 pages.

Hellerstein, L., et al., "Rehabilitative Optometric Management of a Traumatic Brain Injury Patient," Journal of Behavioral Optometry, 1994, 6 pages.

Hellerstein, L., et al., "Vision profile of patients with mild brain injury," Journal of the American Optometric Association, 1995, 7 pages.

Hellerstein, L., et al., "Visual Rehabilitations for Patients with Brain Injury," 2011, 31 pages.

Ilg, U., "Slow Eye Movements," Progress in Neurobiology, 1997, 37 pages.

Kowal, L., "Ophthalmic manifestations of head injury," Australian and New Zealand Journal of Opthalmology, 1992, 6 pages.

Krasnow, D., "Fusional Convergence Loss Following Head Trauma: A Case Report," Binocular Vision and Perception, 1982, 2 pages.

Krauzlis, R., "Recasting the Smooth Pursuit Eye Movement System," The American Physiological Society, 2004, 13 pages.

Krohel, G., "Posttraumatic Convergence Insufficiency," Annals of Ophthalmology, 1986, 3 pages.

Mack, W., et al., "Pupillary Reactivity Upon Hospital Admission Predicts Long-term Outcome in Poor Grade Aneurysmal Subarachnoid Hemorrhage Patients," Neurocrit Care Society, 2008, 6 pages.

McKee, A., et al., "The spectrum of disease in chronic traumatic encephalopathy," A Journal of Neurology, 2012, 22 pages.

(56) References Cited

OTHER PUBLICATIONS

Meeker, M., et al., "Pupil Examination: Validity and Clinical Utility of an Automated Pupillometer," Journal of Neuroscience Nursing, 2005, 7 pages.
Mohan, K., et al., "Retinal Ganglion Cell Damage in an Experimental Rodent Model of Blast-Mediated Traumatic Brain Injury," Invesitgative Ophthalmology and Visual Science, 2013, 11 pages.
Moller, F., et al., "Binocular quantification and characterization of microsaccades," Graefe's Arch Clin Exp. Ophthalmol, 2002, 6 pages.
De Xivry, J., et al., "Saccades and pursuit: two outcomes of a single sensorimotor process," The Phsyiological Society, 2007, 13 pages.
Ritter, A., et al., "Brain Stem Blood Flow, Pupillary Response, and Outcome in Patients with Severe Head Injuries," 1999, 9 pages.
Scheiman, M., et al. "A Randomized Clinical Trial of Treatments for Convergence Insufficiency in Children," American Medical Association, 2005, 11 pages.
Scheiman, M., et al. "Randomised clinical trial of the effectiveness of base-in prism reading glasses versus placebo reading glasses for symptomatic convergence insufficiency in children," 2005, 6 pages.
Scheiman, M., et al. "A Randomized Clinical Trial of Vision Therapy/Orthoptics versus Pencil Pushups for the Treatment of Convergence Insufficiency in Young Adults," Optometry and Vision Science, 2005, 13 pages.
Scheiman, M., "Randomized Clinical Trial of Treatments for Symptomatic Convergence Insufficiency in Children," American Medical Association, 2008, 14 pages.
Simkhovich, D., et al., "Successful Oculomotor Auditory Feedback Therapy in an Exotrope with Acquired Brain Injury," Journal of Behavioral Optometry, 1996, 4 pages.
Soden, R., et al., "A Case in Point: An Optometric Approach to the Treatment of a Non-Comitant Deviation," Journal of the American Optometric Association, 1983, 5 pages.
Stelmack, J., et al., "Visual function in patients followed at a Veterans Affairs polytrauma network site: An electronic medical record review," Optometry, 2009, 6 pages.
Suchoff, I., et al., "The occurrence of ocular and visual dysfunctions in an acquired brain-injured patient sample," Journal of the American Optometric Association, 1999, 9 pages.
Taylor, W. et al., "Quantitative pupillometry, a new technology: normative data and preliminary observations in patients with acute head injury," J. Neurosurg., 2003, 9 pages.
Padula, W., et al., "Head Injury Causing Post Trauma Vision Syndrome," 1988, 6 pages.
Application No. 15755281.1, European Extended Search Report, Mar. 13, 2018, 9 pages.

* cited by examiner

SYSTEM FOR TRAUMATIC BRAIN INJURY DETECTION USING OCULOMOTOR TESTS

CROSS-REFERENCE TO RELATED APPLICATIONS

This application claims priority to U.S. Provisional Patent Application Ser. No. 61/946,361, filed Feb. 28, 2014, the contents of which are incorporated by reference herein.

BACKGROUND OF THE INVENTION

1. Field of the Invention

The present invention relates generally to the field of measuring neurological impairment. The present invention specifically concerns presenting a battery of visual tests and recording a subject's eye position, eye movement, pupil dilation and pupil constriction to measure the severity of any traumatic brain injury.

2. Description of Related Art

Traumatic brain injury can be caused by head trauma after impact. The rapid acceleration or deceleration of the brain within the cranial vault, or absorption of a shock wave can cause the brain to impact the inside of the skull. These forces can also cause stretching and/or shearing of axonal tracts (tearing of connections between neuronal cells), which can trigger secondary neurodegenerative damage and maladaptive plasticity leading to chronic neurological dysfunction. The physiological effects resulting from these injuries can be detected immediately in some cases, but can also develop slowly over minutes, hours, weeks, months, or even years post-injury. Pathological processes can evolve slowly, making them difficult to detect in stages when interventions are most effective. Mild Traumatic Brain Injuries (mTBI) can result in post-concussion syndrome and impairment in cognitive domains such as memory, processing speed, affect, impulse control, prediction/planning and other executive functions as measured by traditional neuropsychological instruments. Acute physiological changes (e.g. inflammation) following mTBI may also make an individual more susceptible to a subsequent impact due to poor judgment or slower reaction times. These repeated impacts may, in turn, make an individual more susceptible to chronic neurological injury. Therapeutic options may be developed to prevent chronic neurological damage if we can identify reliable quantitative markers (changes in physiological and neurobehavioral responses) associated with mTBI. These quantitative measures could also be used in conjunction with acceleration measurements to identify those types of impacts associated with acute and chronic neurological injury. However, there are currently no devices capable of accurately and objectively tracking subtle changes in neurophysiological status associated with either mTBI or systems that accurately measure angular acceleration of the head correlated with mTBI biomarkers.

There is a critical need to identify a sensitive, rapid, easily obtainable biomarker to serve as an objective indicator of when an athlete should be withheld from play and when they can return to normal play in order to avoid permanent traumatic brain injury. Repeated concussive and even subclinical exposures to head trauma can produce a spectrum of chronic traumatic encephalopathy (CTE), resulting in stress points of damage in the brain, ranging in severity from mild cognitive impairment to severe dementia, disinhibited violent outbursts, motor dysfunction, reduced quality of life and even suicide. Oculomotor reactions in response to a pulse of light will reflect the status of the central nervous system following head trauma. Oculomotor reactions integrate a chain of neural events mediated by nerves passing through brain areas commonly affected by acute head trauma, and may also be affected chronically with repeated, mild head trauma which can by cumulative. This invention aims to show that the pupil light reflex and other oculomotor tests, unlike other measures of head trauma, are sensitive to acute, subclinical concussive forces and may also be used to inventory cumulative effects of mild head trauma over time, which fulfills a critical need in contact sports.

SUMMARY OF THE INVENTION

Embodiments of the claimed invention comprise an apparatus and method for measuring levels of neurological impairment. The invention may be used in the detection of traumatic brain injury or other neurological defects. The invention may also be used to detect alcohol or drug-related impairment.

Exemplary embodiments include an apparatus for quantifying a level of neurological impairment comprising: a portable housing; a microcontroller coupled to the housing; a light source coupled to an interior of the housing and operably coupled to the microcontroller; and a first camera and a second camera coupled to the interior of the housing and operably coupled to the microcontroller. In certain embodiments, the housing is adapted to fit over a user's eyes and block external light from reaching eyes of a user; the light source is operable to emit light in a field of vision of the user; the first camera is operable to record a direction, a movement, and a dilation of a right pupil of the user; and the second camera is operable to record a direction, a movement, and a dilation of a left pupil of the user. In particular embodiments, the microcontroller is configured to: control movement of the light source at a velocity of less than thirty degrees per second; control the light source to flash in a first pattern; and control the light source to flash in a second pattern that is the reverse of the first pattern.

In specific embodiments, the microcontroller is configured to measure the amount of time it takes the user to track the light source when the light source is flashed in the second pattern. In certain embodiments, the microcontroller is configured to: control the light source to emit a first flash of light into a right eye of the user; and control the light source to emit a second flash of light in a left eye of the user. Particular embodiments further comprise an external display coupled to an exterior of the housing, where the external display is operable to display a numeric score indicative of a level of impairment. In specific embodiments, the first and second cameras are operable to detect infrared light. In some embodiments, the light source comprises LEDs operable to emit light having a wavelength of about 400-500 nm, or more particularly 420-490 nm, or still more particularly 450-480 nm.

In certain embodiments, the microcontroller is configured to: control the first camera to record a direction, a movement, and a pupillary response of a right pupil of the user for at least two seconds; and control the second camera to record a direction, a movement, and a pupillary response of a left pupil of the user for at least two seconds. In particular embodiments, the pupillary response of the right and left pupils comprises a percent dilation or constriction, a time constant for dilation or constriction, a duration of dilation or constriction, a rate of dilation or constriction. In specific embodiments, the apparatus is configured to measure an orientation of a right pupil of the user and an orientation of a left pupil of the user.

Exemplary embodiments include a method of quantifying a level of neurological impairment comprising: emitting a first flash of blue, red, and/or white light into a user's left eye; tracking a movement of a user's left pupil for at least two seconds; emitting a second flash of blue, red, and/or white light into a user's right eye; tracking a movement of a user's right pupil for at least two seconds; and calculating a numeric score indicative of a level of impairment based upon the movement of the user's pupils. In certain embodiments, the first and second flashes of white light have an intensity of about 0-200 foot candles and a duration of about 0-10 seconds, or more particularly an intensity of about 50-150 foot candles and a duration of about 0-5 seconds, still more particularly an intensity of about 100 foot candles and a duration of about 0.2 seconds. In particular embodiments, the movement of the user's left and right pupils are tracked for greater than one second, and more particularly tracked for about three seconds. In specific embodiments, the movement of the user's left and right pupils are tracked using infrared light. Certain embodiments further comprise adapting a housing is to fit over the user's right and left eyes and block external light from reaching the user's right and left eyes. In particular embodiments, the orientation of the user's pupils is measured using infrared light.

Exemplary embodiments include a method of quantifying a level of neurological impairment comprising: emitting a flash of red or white light into a user's eyes; measuring a user's pupil diameters about at least one second after the flash; waiting until the user's pupil diameters return to a steady state dark adaptation diameter; emitting a flash of bluelight into the user's eyes; measuring the user's pupil diameters at least four seconds after the flash; and calculating an isolated melanopsin response by comparing a user's pupillary response after the blue light flash with the user's pupillary response the red or white light flash. In particular embodiments, the diameter of the user's pupils is measured using infrared light.

Certain embodiments include comparing the user's pupillary responses after the flash of red or white light and after the flash of blue light comprises measuring the pupil diameters at a sampling rate of greater than 50 Hz, or more particularly greater than 60 Hz. In specific embodiments, the flashes of light have an intensity of about 2.6 log cd/m² and a duration of about 1000 milliseconds. Particular embodiments further comprise adapting a housing is to fit over the user's eyes and block external light from reaching the user's eyes.

The invention comprises a portable housing, a microcontroller, a set of light emitting diodes, and cameras. The housing is adapted to fit over a user's eyes and block all external light from reaching the eyes. The set of light emitting diodes is operable to emit light in the user's field of vision. The cameras are operable to detect the orientation, movement, and contraction and dilation of the user's pupils.

In some embodiments, the invention further comprises a display that returns a numeric score that indicates a level of neurological impairment. In some embodiments, the cameras are operable to detect infrared light. In some embodiments, the set of light emitting diodes includes diodes operable to emit light having a wavelength of about 450-480 nm. In some embodiments, the invention further comprises a RFID Bluetooth device that is operable to identify users of the invention.

The invention comprises emitting light into a user's eyes, measuring an orientation of the user's pupils, measuring a contraction and dilation of the user's pupils in darkness and in response to a light, and calculating a numeric score indicative of a level of neurological impairment based upon the orientation, size, contraction and dilation of the pupils.

The invention comprises initially measuring the pupil size in darkness, the contraction dynamics in response to an emitted light and the subsequent dilation of the user's pupils after terminating the emission of light and calculating a numeric score indicative of a level of impairment.

The invention comprises emitting light from a first position, terminating the emission of light, emitting light from a second position, tracking the movement of the user's eye position by tracking the pupil outline from the first position to the second position, and calculating a numeric score indicative of a level of impairment.

The invention comprises moving a light around a display, tracking the movement of a user's pupil outline and size, and calculating a numeric score indicative of a level of impairment.

The invention comprises emitting a flash of white light having an intensity of about 100 footcandles and a duration of about 0.2 seconds, tracking the movement of a user's pupil for about three seconds, and calculating a numeric score indicative of a level of impairment. The invention further comprises testing the left eye and the right eye of the user separately.

The invention comprises emitting light from a light source at the edge of a user's field of vision that is below the intensity of human detection, increasing the intensity of the light, measuring the time elapsed until the user's eyes (pupil location) are oriented toward the light source, and calculating a level of impairment.

The invention comprises emitting a flash of white or red light into a user's eyes, measuring the user's pupil diameters about six seconds after the flash, waiting until the user's pupils return to a steady-state dark adaptation diameter, emitting a flash of blue light into the user's eyes, measuring the user's pupil diameters about six seconds after the flash, and calculating an isolated melanopsin response by subtracting the user's pupil diameter measurement after the blue light flash from the user's pupil diameter measurement after the red light flash. The invention further comprises measuring the pupil diameters at a sampling rate of about 60 Hz. The invention further comprises emitting the flashes of light at an intensity of about 2.6 log cd/m². The invention further comprises emitting the flashes for a duration of one second.

The invention comprises emitting light from a first location, emitting light from a second location, tracking the movement of the user's left pupil and tracking the movement of the user's right pupil from the first location to the second location, and calculating a level of impairment based upon the differential movement of the two eyes by comparing the position of the left pupil and the right pupil at different gaze locations.

The invention comprises tracking a movement of the user's eyes by monitoring the pupil position to a memorized location of a light stimulus emitted, and calculating a level of neurological impairment.

The invention comprises emitting light at a location on the edge of the display, tracking the amplitude, direction and accuracy of a user's eyes by monitoring the pupil position to a location imagined by the subject to be in a position opposite of the emitted light location, and calculating a level of neurological impairment.

The invention comprises emitting lights flashing at a frequency of about 1 to 100 Hz at the four corners of a display; reducing or increasing the frequency of a randomly selected light relative to the other lights; measuring an orientation of the user's pupils; measuring the frequency of the emitted light at which the user's eyes are oriented toward the randomly selected light which appears to flicker at a rate different from the other emitted lights; calculating a level of neurological impairment based upon the measured frequency.

The invention further comprises measuring the contraction, dilation, orientation, and movement of the user's pupils using infrared light. The invention further comprises utilizing recognition of iris features to identify users. The invention further comprises taking a baseline measurement of a user's performance, testing the user again after a head trauma, and calculating a level of neurological impairment by comparing the user's status after the trauma to the baseline measurement.

As used herein the specification, "a" or "an" may mean one or more. As used herein in the claim(s), when used in conjunction with the word "comprising", the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

Figure 1A:
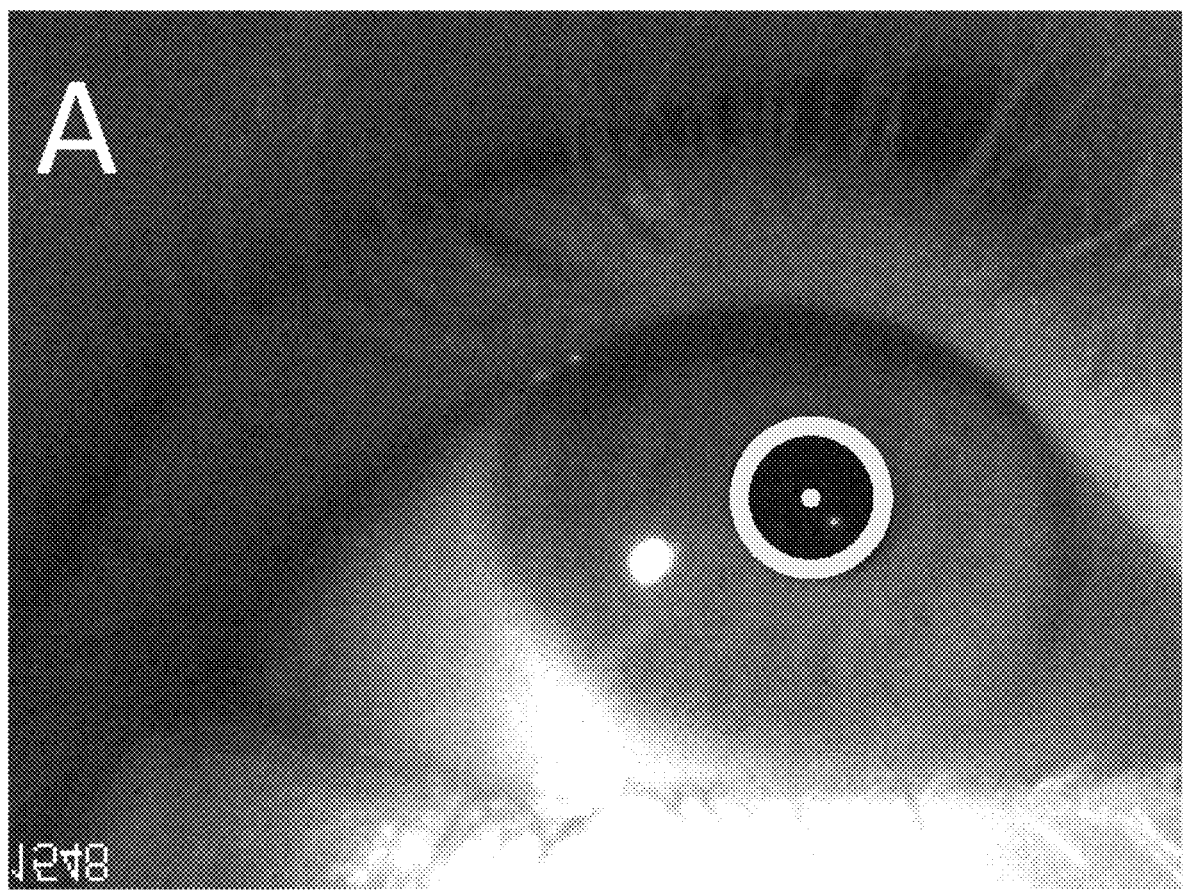
FIG. 1A shows an infrared image of an eye with pupil border outlined by automated software analysis and depicted by a thick white border line.
Figure 1B:
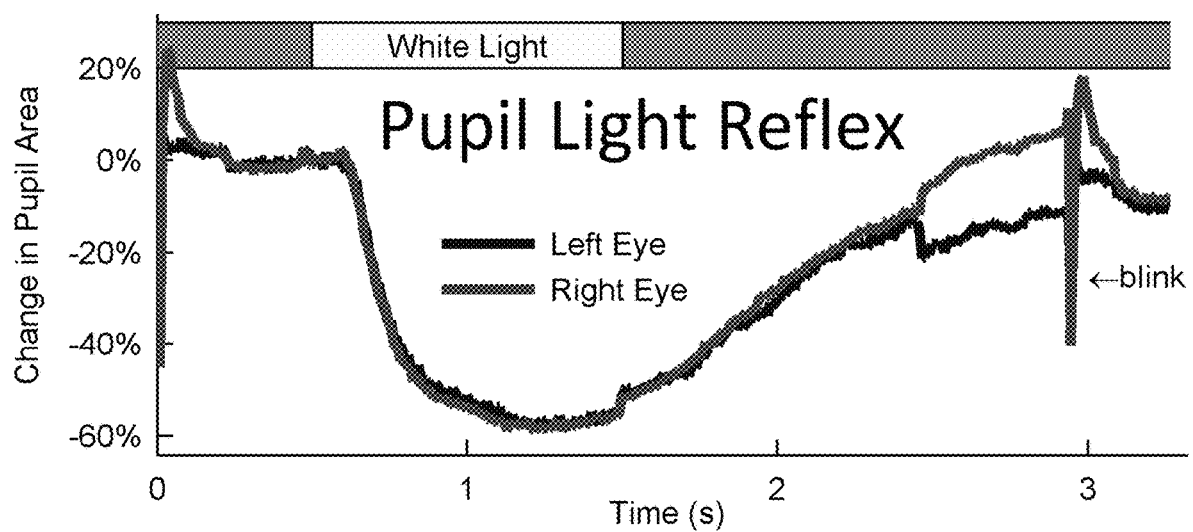
FIG. 1B shows a graph of pupil light reflex data in response to a white light.
Figure 1C:
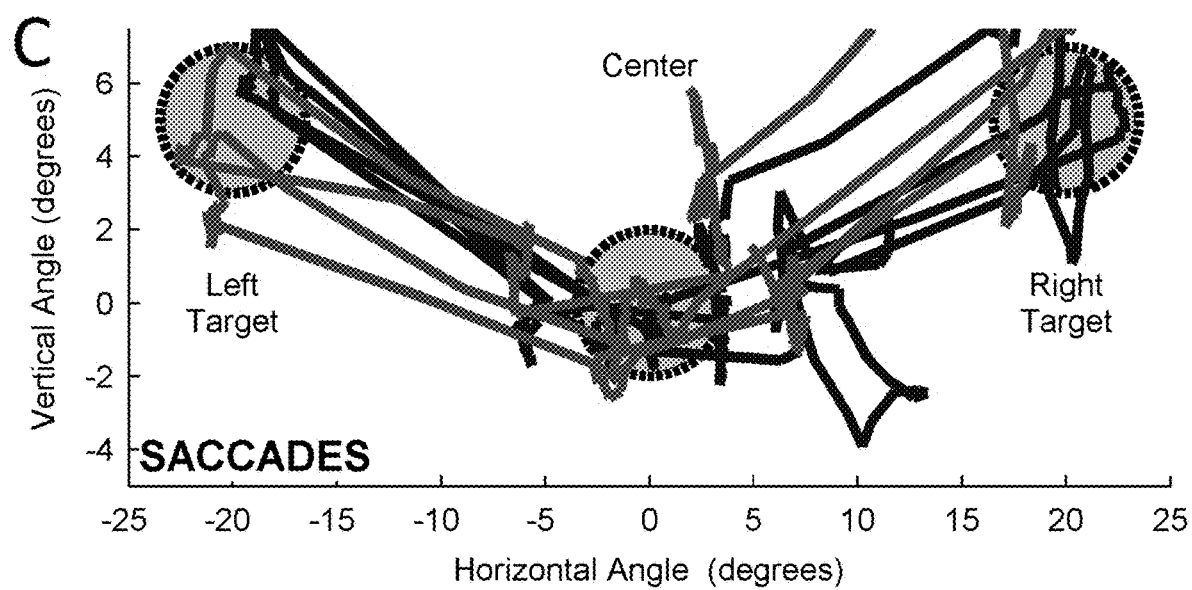
FIG. 1C shows a plot of eye position during saccades testing.
Figure 1D:
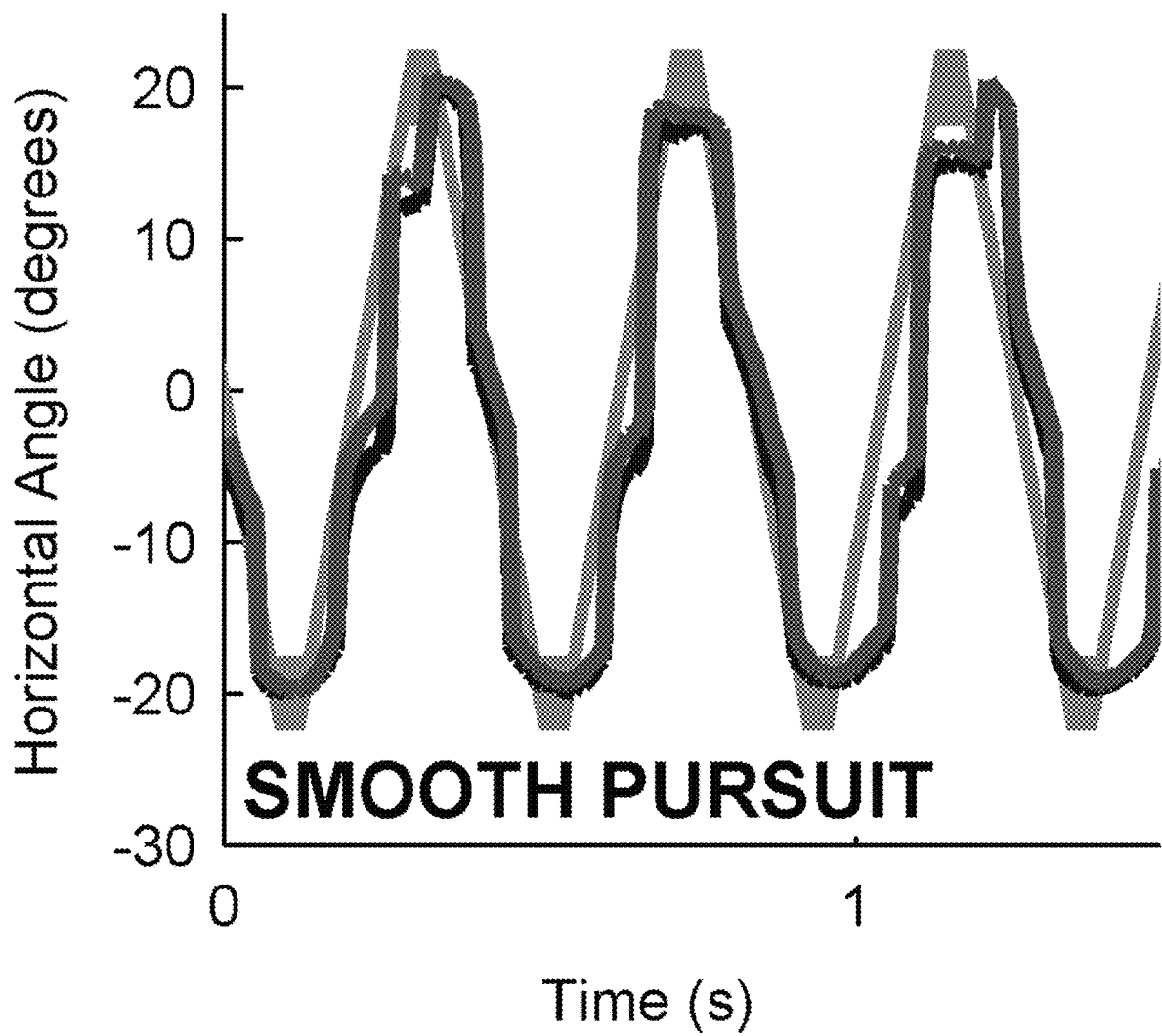
FIG. 1D shows a plot of eye position during smooth pursuit testing.

Exemplary embodiments of the present disclosure include an apparatus (also referred to herein as the "NeuroTriage Headset"). Exemplary embodiments are designed to detect physiological changes associated with mild traumatic brain injuries. Exemplary embodiments are designed to measure changes in neurological function following mTBI and compare those measurements to baseline measures to detect changes in neurological status. Embodiments of the invention may include web based applications that will allow the data to be collected and analyzed in real time. This will allow individuals and their health care teams to identify changes in neurological status compared to baseline measurements. These devices may predict the long-term neurological consequences of mTBI. Exemplary embodiments may prove useful in providing the information needed to develop strategies, rules, and interventions to minimize neurological damage due to head impacts.

NeuroTriage Headset and Method of Evaluation. Physicians have long used a battery of oculomotor observations in the evaluation of neurological status. These observations range from eye reflexes, such as the pupillary light reflex, eye pursuit, saccadic and vergence movements, and visual performance tasks that require significant cognitive load (i.e., memory and concentration). Recently it has been shown that constriction latency, average constriction velocity, and dilation velocity obtained from the pupillary light reflex are indicators of mTBI in blast-exposed individuals (Capo-Aponte et al., 2013). These measures are quantifiable and repeatable, providing a method for following changes in neurological status after an impact. These oculomotor tests can be sensitive to detecting changes in neurological status because the oculomotor system integrates with multiple brain networks and substrates that span both basic perceptual processing (reflexes) and tasks involving higher-order cognitive load (lower- and higher-order processing; levels of difficulty). The visual system interacts with virtually all other brain systems and, as a result, oculomotor-visual tests have a high likelihood of detecting dysfunctions across multiple brain regions and processing pathways.

Testing was performed to investigate the function of melanopsin-expressing intrinsic photosensitive retinal ganglion cells (ipRGCs) in normal subjects, and in multiple sclerosis (MS) patients with a history of optic neuritis. It is theorized that patients with neurological conditions other than MS, including mTBI, may show dysfunction in the melanopsin mediated pupillary light reflex. Fifteen control individuals (n=30 eyes) and 24 patients (n=48 eyes) with multiple sclerosis were recruited for testing. All patients underwent pupillometry testing with red and blue light stimuli to observe both the non-melanopsin and melanopsin-mediated (with the latter characterized by a sustained pupillary constriction period in conjunction with a protracted dilation phase following light stimulus cessation) pupillary light reflexes. The tests further employed optical coherence tomography (OCT) retinal segmentation techniques, in order to characterize the relationship between thickness of the ganglion cell layer and inner plexiform layer (GCL+IPL) and the disposition (normal vs abnormal) of the melanopsin-mediated pupillary response.

The tests confirmed a direct and significant correlation between GCL+IPL thickness and the melanopsin response (p<001). Further, a significantly diminished melanopsin response was associated with MS eyes categorically designated with a history of acute optic neuritis (AON) when compared to MS patient eyes with no history of AON (p=0.005). More objectively, when compared to MS eyes with normal GCL+IPL thickness, the melanopsin response was significantly attenuated in MS eyes exhibiting GCL+ IPL thickness reductions (p<0.0001). Notwithstanding the high incidence of subclinical optic neuropathy in the fellow eye of MS patients with a history of AON in the other eye, we performed an intra-subject, inter-eye asymmetry comparative analyses, which revealed a significant reduction in GCL+IPL thickness in eyes with a history of AON (p=0.01 for both).

Perhaps the greatest advantage of oculomotor testing is that it is non-invasive, easy to analyze, and can be done on the sideline, on the side of the road, or in the clinic, requiring little effort on the part of the patient. For example, simple eye tracking assessment is currently used by trained professionals for assisting with the detection of TBI and for field sobriety testing. Quantifiable and observable oculomotor system dysfunction has been demonstrated in a number of neurological disorders and conditions, including several neurodegenerative diseases, pharmacological impairment, and blast induced mTBI. It is likely that an efficient, automated, and on-field battery of these tests that quantify physiological responses will be sensitive to detection of mTBI due to head impacts as well. The following describes a series of automated tests that can be performed with the NeuroTriage Headset. The testing should take less than five minutes to perform.

In preferred embodiments, the NeuroTriage Headset uses two USB3 cameras, which may be obtained from the Imaging Source, that capture video at 150 Hz to track pupil diameter and position. In preferred embodiments, these cameras are mounted on a heads-up display and are controlled via an ATmega32U4 microcontroller. The microcontroller may be mounted on a display board that controls the presentation of stimuli. The NeuroTriage Headset includes light emitting diodes (LEDs) to emit light into the wearer's eyes. The LEDs may emit light having a wavelength between 250-950 nm. In preferred embodiments, the system includes infrared, white, red, blue, and green LEDs. In other embodiments, the system includes LEDs emitting light having a wavelength between 450-480 nm. It appears that this 450-480 nm wavelength activates melanopsin cells and the retinohypothalamic tract. This visual pathway is distinct from the pathway activated by the normal rod and cones. As a result it may be a more sensitive biomarker for detecting brain injuries or detecting different type of injury. A 3-8 multiplexor may be used to present the smooth pursuit target (eight LEDs light up in order). In some cases a 4-16 multiplexor is used. A standard visual display could be used such as from a phone, tablet, laptop or other screen. Other LEDs may be positioned at the corners for saccade tests. Two cameras, separated by approximately 3.5 inches, are mounted approximately two inches from the eyes. The NeuroTriage Headset includes software that provides a custom interface for stimulus presentation and image capture. The software accurately analyzes the eyelid borders, pupil borders, and limbus in each video frame, from which eye, lid, and pupil movement and gaze direction can be accurately determined. In preferred embodiments, the software produces a score, e.g., 1 to 100, indicating the level of neurological impairment. In some embodiments, the NeuroTriage Headsets utilize iris features and an RFID Bluetooth device to ensure proper identification of all subjects during initial and repeat testing.

Figure 2:
FIG. 2 shows a perspective view of a headset according to exemplary embodiments of the present disclosure.
Figure 3:
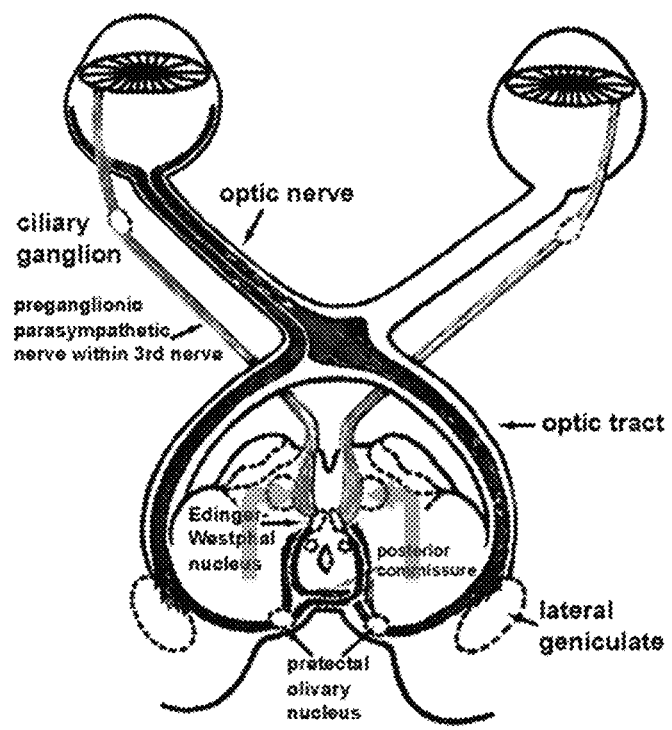
FIG. 3 shows a diagram of the pupil light reflex pathway.

In preferred embodiments, the NeuroTriage Headset is in the form of a portable headset or set of goggles. FIG. 2 depicts the NeuroTriage Headset. The housing of the NeuroTriage Headset blocks external light such that the only light received by the user's eyes is from the NeuroTriage's LEDs. Various tests may be employed by the NeuroTriage Headset, including but not limited to Pupil Reflex, Saccades, Smooth Pursuit, and Critical Flicker Fusion. These tests are described in more detail below.

Pupil Reflex: The pupil light reflex is the dilation and constriction of the pupil in response to changes in lighting. This reflex integrates neuronal processes mediated by brain areas and neuronal tracts commonly affected by acute head trauma. Disruption at any step can result in abnormal reflex functionality (Chen et al., 2011; Taylor et al., 2003; Ritter et al., 1999; Meeker et al., 2005; Mack et al., 2008; Mohan et al., 2013). Recent studies have demonstrated that the pupil light reflex is even sensitive to acute, subclinical concussive forces (Capo-Aponte et al., 2013). It has the potential as an inventory tool for the cumulative effects of mild head trauma over time. This approach would fulfill a critical need for testing individuals with repeated exposures to mTBI. Unlike eye movement measures, the light reflex is involuntary, so it can be measured without dedicated patient cooperation.

Figure 5:
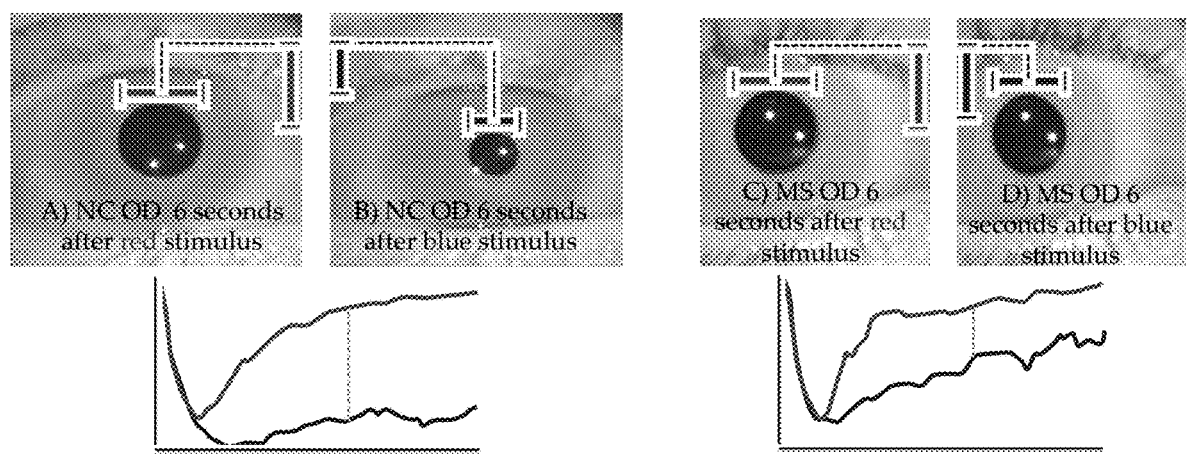
FIG. 5 shows images of pupils and their movements in response to red and blue light stimuli.

FIG. 5 is a schematic of the pupillary light reflex pathway, including a) the afferent limb (retina, including the melanopsin intrinsically photosensitive retinal ganglion cells, optic nerve, chiasm, optic tract and brachium of the superior colliculus), b) the inter-neuron consisting of nerves in the pretectal olivary nucleus in the midbrain which provide input via the posterior commissure to c) the efferent limb. The efferent limb consists of the pre-ganglionic parasympathetic neurons in the Edinger Westphal Nucleus. These pre-ganglionic fibers then travel within the oculomotor nerve and then into the orbit. After synapsing in the ciliary ganglion, the post-ganglionic parasympathetic neurons innervate the iris sphincter muscle. Supra-nuclear fibers from the reticular activating formation in the pons ascend into the midbrain (red arrows) to modulate the response of the preganglionic parasympathetic neurons in the Edinger Westphal Nucleus during states of wakefulness and sleep. The sympathetic nerves, which innervate the iris dilator, also modulate pupil size and dilation. Concussion may theoretically affect the pupil light reflex throughout any portion of this pathway. However, the most likely location is within the midbrain pathways and connecting neurons that modulate the pupil motor center. By recording both pupils at the same time in response to a light pulse given to the right eye and then to the left eye, the location of disturbances to the pupil pathway can be isolated.

Two light input retinal pathways can be interrogated using the pupillary response, in addition to the central nervous system (CNS) pathways modulating the neural integration of the pupil light reflex that appear to be affected by TBI. The first pathway involves activation of the rod and cone photoreceptors using low intensity light to cause a standard transient pupil light reflex. The second pathway involves direct activation of melanopsin-containing retinal ganglion cells by bright blue light and results in a longer-lasting pupil contraction after the light is terminated. This pathway appears to be distinct from the rod and cone mediated pupillary response, which is more transient, as discussed above. The tests would use white light, red light and blue light separately to measure pupil dynamics. Changes in one or the other may indicate brain injuries in different neural pathways.

Few studies have investigated the pupillary light reflex specifically for mTBI assessment. The dynamics of pupil movement in response to a light pulse have been condensed into a single parameter of pupil reactivity, termed the Neurological Pupil Index (NPI) which has a value ranging from zero (non-reactive) to five (most reactive). The NPI incorporates a z-scale sum of pupil size, iris mechanics, contraction amplitude, latency, contraction velocity, and dilation velocity from the normal population (3). It has been determined from previous studies of intensive care patients with traumatic brain injury (TBI) compared to normal subjects that an NPI of greater >3 is normal and <3 is associated with brain dysfunction and higher risk of morbidity (3-5). Preliminary studies have shown that NPI possesses low variability in test-retest measures of normal participants: one hundred measurements from normal eyes (patients aged 18-30) resulted in a mean NPI of 4.2±0.32, and two standard deviations from ten patients retested over five days was only 0.27 NPI units. Therefore, the NPI provides a reproducible, repeatable measurement of pupil response dynamics and a basis for defining significant change between test measurements in subjects being followed after mild TBI. Chen et al. (2011) demonstrated that a low NPI score was significantly correlated with abnormal intracranial pressure in more severely injured patients admitted to hospital intensive care units (two-tailed t-test, p=0.0014). In a number of cases, a drop in the NPI preceded the rise in intracranial pressure. In a recent publication, warfighters exposed to explosions were shown to have differences in constriction latency, average constriction velocity, dilation velocity, and 75% recovery time using a pupil dilation test (Capo-Aponte et al., 2013).

An important innovation was realized from the results of a recent pilot led by the current investigators, which validated the usefulness of the NPI as an acute biomarker of TBI predicting neurological outcome. The NPI was recorded in 128 patients being evaluated for acute TBI. An abnormal NPI was predictive of outcome and seriousness of acute traumatic brain injury. Specifically, patients with an NPI≤3 (compared to patients with NPI>3) were found to have a significant likelihood of 1) worse Glasgow Coma Scale, 2) head CT scan abnormalities, 3) need for neurosurgical intervention, 4) longer length of hospitalization, and 5) need for skilled care after discharge. These results showed that the NPI is a significant biomarker of acute brain trauma that is predictive of outcome and the need for further evaluation. It is from this pilot data that the idea for the present study was conceived. These results are relevant to assessment of traumatic brain injury from a variety of causes, including blunt trauma from falls and motor vehicle accidents, blast-related TBI, and in the current application, to sports-related head trauma. Unlike other causes of TBI, the use of the NPI to evaluate sports related head trauma might even be more sensitive, since a baseline NPI or pregame NPI can be compared to measurements during play. For example, after sustaining a significant head impact event during play, the absolute value of the NPI may still be in the normal range, but the change from baseline may be greater than expected by chance, indicating a severe enough injury to withhold an athlete from play. Therefore, if the change in NPI reflects the severity of brain insult, then acute changes in the NPI and the duration of such changes may provide a viable biomarker for an on-field assessment of head trauma and influence decisions on safe return to play. If changes of NPI are sustained, then there may also be a use for monitoring cumulative effects of injury and relating these to assessments of cognitive function and structural changes in the brain and retina. A recent study conducted on veterans with a history of TBI compared to age matched veterans without TBI revealed permanent thinning of the inner retinal layers containing neurons which make up the optic nerve in at least 25% of eyes. These patients had no obvious abnormality on eye exam, indicating that head trauma can result in structural loss of nerves in the retina, which may be a surrogate marker for permanent brain effects, also demonstrated in our preclinical murine models of TBI. Non-invasive optical coherence tomography imaging (OCT) of the layers of the retina is easily obtained without pupil dilation and has no risk associated with it, making it a suitable biomarker to inventory chronic, cumulative effects of brain trauma causing permanent loss of nerves.

In the preferred embodiment, the NeuroTriage Headset provides a 100 footcandle bright white, LED flash (group of four light emitting diodes for stimulating each eye) for 0.2 seconds and records the resulting pupil movements over the next three second time window. It has been previously shown that the NPI is not dependent upon the background lighting condition. All measurements may be taken under photopic background conditions, primarily outdoors. The right and left pupil movements may be recorded for each right eye and left eye light stimulus, generating a right and left pupil NPI for each light stimulus, for a total of 4 NPI determinations collected at each testing time.

In another embodiment, the NeuroTriage Headset provides a 2.6 log cd/m² LED flash using 1000 millisecond stimuli duration in each eye individually. The device may use both red LED (622 nm) and blue LED (463 nm) variants. Each stimulus should be timed so that the pupils return to their steady-state dark adaptation diameter in between each of the stimuli. Pupilary diameter may be captured at a sampling rate of 60 Hz. An isolated melanopsin response may be quantified by measuring the normalized pupil diameter six seconds after the red light stimulus and subtracting the normalized pupil diameter six seconds after a corresponding blue light stimulus of matched intensity. The system may calculate the activity of the melanopsin-driven retinomesencephalic tract, $RM_{mel}$, using the following equation:

$$RM_{mel} = \frac{d_{R6}}{d_{R0}} - \frac{d_{B6}}{d_{B0}}$$

where $d_{R6}$ is the pupil diameter during the red stimulus at six seconds, $d_{R0}$ is the pupil diameter immediately prior to red stimulus, $d_{B6}$ is the pupil diameter during the blue stimulus at six seconds, and $d_{B0}$ is the pupil diameter immediately prior to blue stimulus. The system may also calculate the transient pupil response, $P_{TR}$, using the following equation:

$$P_{TR} = \frac{d_{E0} - d_{Bmin}}{d_{E0}}$$

where $d_{Bmin}$ is the absolute minimal pupil diameter during the blue stimulus.

Figure 4:
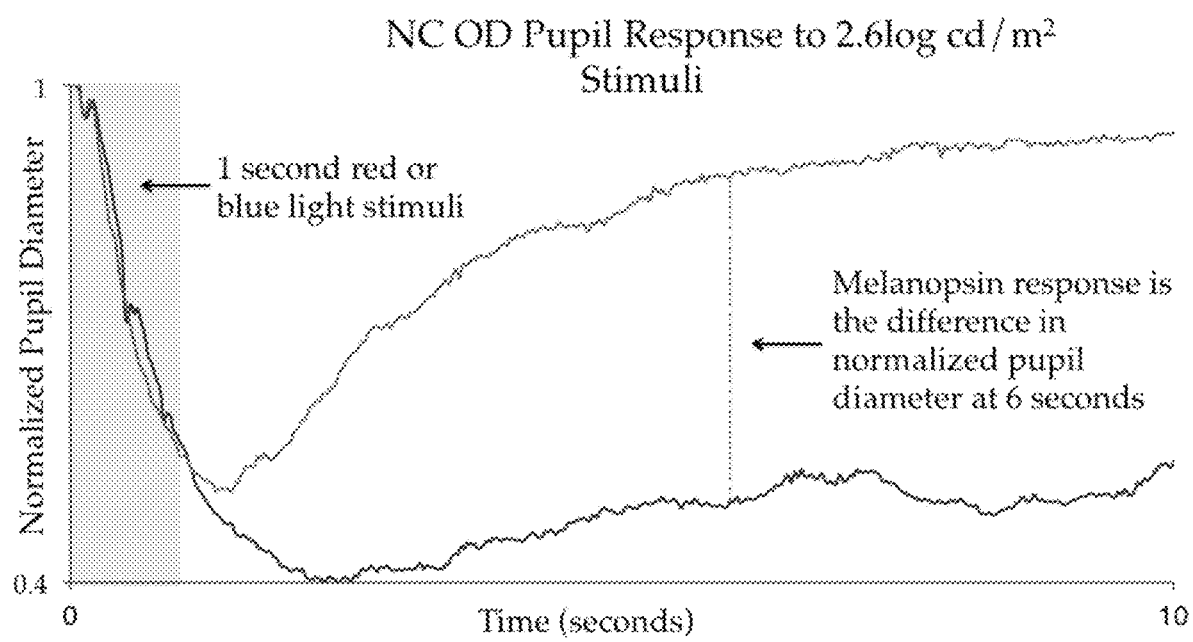
FIG. 4 shows a graph of pupil response to red and blue light stimulus over time.

FIG. 4 shows the normalized pupil diameter vs time for a control user. The gray line represents pupil diameter as a function of time for the red stimulus profile. The patient is shown a unilateral red light stimulus of 2.6 log cd/m² for one second. The pupil reaches maximum constriction shortly after the stimulus is removed and returns to baseline over a period of several seconds. The black line represents the same experimental condition, except this time for a blue light stimulus. In this instance, the return from maximum constriction to baseline diameter is prolonged from thirty to sixty seconds. The line drawn at six seconds represents the difference in pupil diameter between the red and blue light stimuli and is what we quantify as the melanopsin response.

FIG. 5 parts A and B show the pupil diameter at six seconds after photopically matched red and blue light stimuli in a normal control. The difference in pupil diameter is the melanopsin response. This is in comparison to parts C and D, which show the same experimental condition except for an MS patient's eye with severe ganglion cell layer (GCL) and inner plexiform layer (IPL) thinning under the same conditions. There is an attenuation of the melanopsin response when compared to the normal control.

Figure 6:
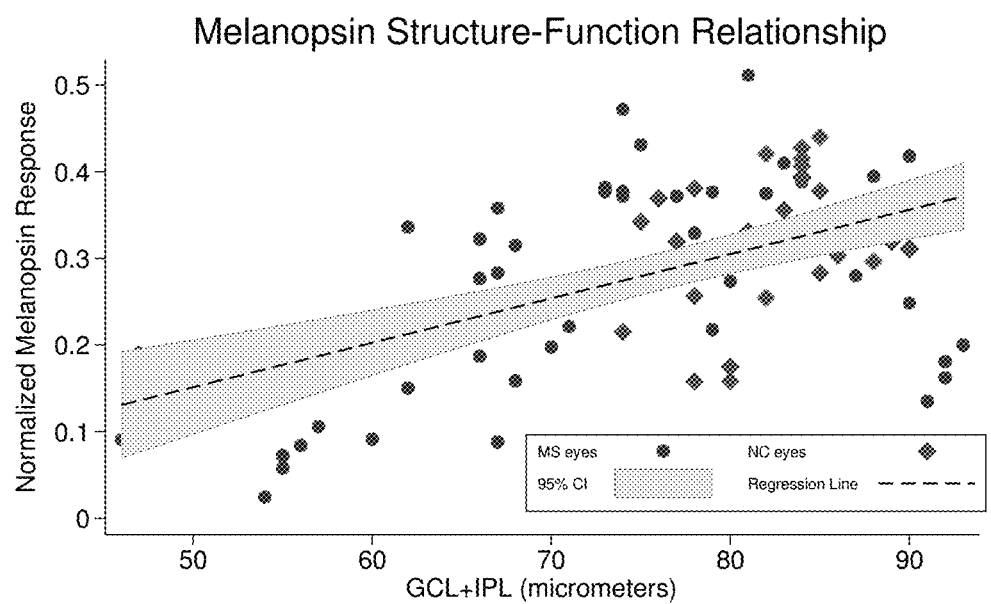
FIG. 6 shows a plot of melanopsin dependent pupil responses as a function of the neural layer thickness of the inner retina in a structure-function relationship.

FIG. 6 is scatterplot and linear regression line show the melanopsin structure-function relationship as a function of normalized melanopsin response by GCL+IPL thickness. A GEE model accounting for age and adjusting for within-patient, inter-eye correlations shows a significant correlation between the melanopsin response and GCL+IPL thickness ($p<0.001$).

Changes in NPI from baseline measurements may be compared among athletes on the sideline immediately following head impact, to those without head impact. In addition, acute changes in NPI may be correlated with a sideline neurologic assessment, SCAT3, in players with and without exposure to head trauma over time.

For each test time, the right and left pupil response is recorded simultaneously for a right eye light stimulus and then for a left eye light stimulus, yielding a total of four NPI measurements. To localize the site of the pupil light reflex pathway affected by acute impact, the four NPI measurements will be grouped in an attempt to isolate afferent, central and efferent locations of modulation by trauma. For example, to identify asymmetry of afferent acute changes in the retina or optic nerve, the right and left pupil NPI may be averaged for the right eye stimulus and compared to the left eye stimulus. Similarly, to identify efferent acute changes along the parasympathetic or sympathetic nerve pathways, the right eye pupil responses may be averaged for the right and left eye stimuli, and left pupil responses will be averaged for the right and left eye stimuli. For centrally mediated changes in NPI, all four determinations may be averaged together for each time point.

Saccade-Tracking: Saccades are fast, simultaneous movements of both eyes in the same direction for the purpose of acquiring an object of interest onto the highest resolving portion of the retina, the fovea. These movements are used to re-fixate on particular objects as the eyes naturally drift, but also to integrate perspective and depth into a scene using binocular viewing. Saccades may be categorized into four main types: visually-guided, memory-guided, predictive, and anti-saccades. Visually-guided saccades move toward a stimulus and may be further bifurcated into self-paced or reflexive movements. Memory-guided saccades do not use a visual stimulus, but rather a memorized stimulus position. Predictive saccades are induced while eyes are tracking a regularly moving object. Anti-saccades are the conscious movement in the opposite direction of a visual stimulus. Damage to specific brain regions have been shown to correlate to a particular type of saccade dysfunction.

During self-paced saccades testing, subjects are directed to shift eye direction between two targets as rapidly as possible. Lights appear simultaneously on the screen and the patient is asked to shift their gaze between the two lights as fast as possible. The system then measures the saccade speed and synchrony along with several other measures including accuracy. If the right and left eyes move at different rates or display other disparities it may also be an indicator of an injury. Studies report fairly strong statistical significance in the number of self-paced saccades between mTBI and control groups ($p=0.003$ for Heitger et al., 2004; $p=0.0016$ for Jacobs et al., 2012). Overall, evidence suggests measuring absolute number of saccades during a self-paced test is an acceptable and rapid approach to screen suspected mTBI patients.

Visually-Guided Saccades: For visually-guided saccades, the system presents a visual stimulus, i.e., turns on one or more LEDs. The system then tracks the movement and position of the user's pupils. A number of studies have reported statistically significant differences in visually-guided saccades parameters for brain-injured groups of mixed severity (Capo-Aponte et al., 2012b; Castro et al., 2012; Heitger et al., 2002; Heitger et al., 2004). Other tested saccade parameters were not significantly different in two additional studies (Heitger et al., 2005 and Kraus et al., 2007).

Memory-Guided Saccades: In a memory guided saccade, the system prompts the user to move his or her eyes to a remembered point, such as the center of the screen, without presenting a visual stimulus. Crevits et al. (2000) reported no significant differences for percent error and latency parameters of memory-guided saccades between intoxicated mTBI patients and control participants. Conversely, Heitger et al. (2006) reported significant differences in directional errors and absolute position errors up to six months post-traumatic brain injury. Significance levels are highest close to the time of injury ($p<0.01$ at one week; $p<0.05$ at 6 months).

Anti-Saccade Testing: For this test, the system presents a stimulus at a random location on the edge of the screen. The individual is asked to look in the opposite direction to an imagined location at the same distance from center as the emitted light. This test requires significant cognitive control and may be highly sensitive to mild brain injuries. While Crevits et al. (2000) reported no statistically significant differences between groups in regard to anti-saccade percent error and latency, the Heitger et al. (2006) study reported latency and absolute positional error abnormalities lasting up to one week and three months post-injury, respectively. Kraus et al. (2007) also reported statistically significant measures of antisaccades (p values ranging from <0.05-0.01), but not gap latency in a sample of mTBI patients.

Smooth Pursuit Eye Tracking with Error Correction: For this task, the system moves a stimulus across the display at various rates. The individual is instructed to follow the stimulus across the screen. The stimulus can move in any direction. Smooth pursuit eye movements allow the direction of gaze to closely track slowly moving targets. Pursuit of targets moving with velocities greater than thirty degrees/second tends to require catch-up saccades to maintain the position of gaze on the moving target. In contrast, targets moving with velocities less than thirty degrees/second provide for smooth pursuit eye movements that require the coordination of many neural systems that are localized to distinctly different areas of the brain. This diverse neural circuitry makes the smooth pursuit cortical network particularly susceptible to impairment from a variety of disorders and conditions. Error correction is then added with this task. The light moves in a predictable pattern then at a random point in time the direction of the pattern is reversed. The amount of time it takes for a user to correctly track the lights moving in the new direction is then measured. In addition to potentially detecting traumatic brain damage, the smooth pursuit system has been shown to be an indicator of abnormal clinical states including post-traumatic stress disorder (PTSD), drug and alcohol abuse, and psychotic symptoms.

Capo-Aponte et al. (2012b) measured a series of eye movement types using conventional eye exam methods in blast-injured patients and controls and found smooth pursuit to be the second most accurate measure to differentiate the two groups (p<0.001). However, the smooth pursuit measure was an "expert rater" scale of smooth pursuit determined by a clinician (Northeastern State University College of Optometry Oculomotor Test), which does not appear to have been validated and the clinician was not masked to the study. Hellerstein et al. (1995) reported smooth pursuit deficiencies using the Southern California College of Optometry (SCCO) technique (p=0.001, Fischer's Test), but not every patient in either mTBI or control groups were assessed. Similarly, Maruta et al. (2010) reported significant differences for intra-individual gaze positional error variability and not horizontal for vertical gains or mean phase of error. The Suh et al. studies (2006a and 2006b) reported that predictive smooth pursuit testing during target blanking is a sensitive indicator of injury leading to attentional and other cognitive deficits. Multiple parameters were reported as statistically different between groups.

Critical Flicker Fusion: The critical flicker fusion test uses four or more LEDs at the corners of the display. All LEDS are flashing at high frequencies that fuse for humans (being perceived as a constant non-flickering light), such as above 40 Hz. The individual is then asked to look at the specific LED that starts perceptibly flashing. The system then randomly reduces the frequency at one of the LEDs that is flickered. When the individual detects the change in the emitted light flicker rate and directs their gaze at that light, the system detects the saccade to that position. The system may run this test several times using adaptive tracking to hone in on the critical flicker fusion frequency.

FIG. 1 shows examples of raw data captured from two cameras that simultaneously track the pupil diameter and gaze direction during slow and fast movements. FIG. 1A shows an infrared eye image with a circle tracking the pupil diameter, and a point marking the pupil centroid. FIG. 1B shows changes in pupil diameters as the NeuroTriage system turns on and off the low intensity white LEDs in the headset. FIG. 1C shows the raw data of the system tracking both pupils during repeated saccadic testing; the eye movements are overlaid on three visual targets. FIG. 1D shows pupil tracking during the smooth pursuit task as right and left eyes track a light moving from left to right.

The inventors have demonstrated that pupillary reflex responses are sensitive markers of acute brain trauma. A recent pilot study validated the usefulness of the NPI as an acute biomarker of more serious TBI and was correlated with indicies of neurological outcome (data not shown). The NPI incorporates a z-scale sum of pupil size, iris mechanics, contraction amplitude, latency, contraction velocity, and dilation velocity from the normal population. The NPI was recorded in 128 patients being evaluated for acute TBI in the University of Iowa Emergency Treatment Center. An abnormal NPI was predictive of outcome and seriousness of acute traumatic brain injury. Specifically, patients with an NPI≤3 (compared to patients with NPI>3) were found to have a significant likelihood of: 1) worse Glasgow Coma Scale, 2) cranial CT scan abnormalities, 3) need for neurosurgical intervention, 4) longer length of hospitalization, and 5) need for skilled care after discharge. These results showed that the NPI is a promising biomarker of acute brain trauma that is predictive of outcome and in need of further evaluation.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Al-Qurainy, *Brit J of Oral and Maxillofacial Surgery.* 32:71-75, 1995.
Anderson, *Brit Orthop J.* 18: 117-120, 1961.
Berne, *J Optom Vis Dev.* 23:13-16, 1990.
Brahm, et al., *Optom Vis Sci.* 86: 817-825, 2009.
Candler, *Br Orthopt J.* 2: 56-62, 1944.
Capo-Aponte, et al., *Mil Med.* 177:804-813, 2012.
Carpenter, Movements of the Eyes. Pion Ltd. London, UK, 1988.
Chen, et al., *Surg Neurol Int.* 2:82, 2011.
Ciuffreda, et al., *Optometry.* 78: 155-162, 2007.
Ciuffreda, et al., *Optometry.* 79: 18-22, 2008.
Cluffreda, et al., *J Beh Optom.* 1:31-37, 1996.
Cohen, *Brain Injury.* 3:187-191, 1989.
Cohen, *J Am Optom Assoc.* 52: 795-800, 1981.
Cohen, *J Am Optom Assoc.* 63: 569-575, 1992.
Cohen, *J Am Optom Assoc.* 7: 831-4132, 1978.
Convergence Insufficiency Treatment Trial Investigator Group, Arch Ophthalmol. 126: 1336-1349, 2008.
Dashnaw, et al., *Neurosurg Focus.* 33: 1-9, 2012.
Gamlin, *Ann NY Acad Sci.* 956:264-272, 2002.
Gianutsos, *Arch Phys Med Rehabil.* 169:513-518, 1988.
Goodrich, et al., *J Rehabil Res Dev.* 44: 929-936, 2007.
Goodrich, et al., *Optam Vis Sci.* 90: 105-112, 2013.
Gould, et al., *Biol Psychiat.* 50:633-635, 2001.
Hellerstein & Freed, *J Beh Optom.* 5:143-148, 1994.
Hellerstein, et al., Understanding and managing visual deficits: a guide for occupational therapists. NJ: Slack, 2011.
Hellerstein, *J Am Optom Assoc.* 66: 634-639, 1995.
Iig, *Prog Neurobiol.* 53: 293-329. 1997.
Korehl, et al., *Ann Opthalmol.* 18:101-104, 1986.
Kowall, *Aut NZ J Opthalmol.* 20:35-40, 1992.
Krasnow, *Optom Monthly.* 18-19, 1982.
Krauzlis, *J Neurophysiol.* 90:591-602, 2004.
Leigh & Zee, Oxford University Press: Oxford, UK, 2006.
Leslie, In: Visual & Vestibular Consequences of Acquired Brain Injury. Santa Ana, Calif.: Optometric Extension Program, 56-76, 2001.
Mack, et al., *Neurocrit Care.* 8:374-9, 2008.
McKee, et al., *Brain.* 136(Pt1):43-64, 2012.
Meeker, et al., *J Neurosci Nurs.* 37: 34-40, 2005.
Mohan, et al., *Invest Ophthalmol Vis Sci.* 54: 3440-50, 2013.
Moller, et al., *Graefes Arch Clin Exp Ophthalmol.* 240:765-770, 2002.

Orban de Xivry, et al., *J Physiol.* 584(Pt1):11-23, 2007.
Padula, *New Eng J Optom.* 16-21, 1988.
Ritter, et al., *Neurosurgery* 44: 941-8, 1999.
Scheiman, et al., *Arch Opthalmol.* 123:14-24, 2005.
Scheiman, et al., *Br J Opthalmol.* 89:1318-23, 2005.
Scheiman, et al., In: Visual and vestibular Consequences of Acquired Brain Injury. Santa Ana: Optometric Extension Program, 2001.
Scheiman, et al., *Optom Vis Sci.* 82:583-95, 2005.
Simkhovich, et al., *J Beh Optom.* 17:93-95, 1996.
Soden, et al., *J Am Optom Assoc.* 54:451-54, 1983.
Stelmack, et al., *Optometry.* 80: 419-424, 2009.
Suchoff, et al., *J Am Optom Assoc.* 70:301-308, 1999.
Taylor, et al., *J Neurosurg.* 98:205-13, 2003.

What is claimed is:

1. An apparatus for quantifying a level of neurological impairment comprising:
   a portable housing;
   a microcontroller coupled to the housing;
   a light source coupled to an interior of the housing and operably coupled to the microcontroller; and
   a first camera and a second camera coupled to the interior of the housing and operably coupled to the microcontroller, wherein:
      the housing is adapted to fit over a user's eyes and block external light from reaching eyes of a user;
      the light source is operable to emit light in a field of vision of the user, the field of vision including: a location;
      the first camera is operable to record a direction, a movement, and a dilation of a right pupil of the user;
      the second camera is operable to record a direction, a movement, and a dilation of a left pupil of the user; and
      the microcontroller is configured to perform a smooth pursuit with error correction task, the smooth pursuit with error correction task including the microcontroller:
         controlling the light source to flash in a first pattern predictably moving in a first direction;
         controlling the light source to flash in a second pattern moving in a second direction that is the reverse of the first direction at a point in time unpredictable by the user after tracking the first pattern, wherein the second pattern interrupts the first pattern at the point in time to cause the user to temporarily lose track of the light source; and
         quantifying the level of neurological impairment based upon at least one of: the recorded direction, movement, or dilation, of the right and left pupils of the user while tracking the first pattern and the second pattern.

2. The apparatus of claim 1, wherein the microcontroller is further configured to control movement of the light source at a velocity of less than thirty degrees per second during the smooth pursuit with error correction task.

3. The apparatus of claim 1, wherein the smooth pursuit with error correction task further includes the microcontroller measuring the amount of time it takes the user to correctly track the light source when the light source is flashed in the second pattern.

4. The apparatus of claim 1, wherein the microcontroller is further configured to perform a pupil reflex task, the pupil reflex task including the microcontroller:
   controlling the light source to emit a first flash of light into a right eye of the user;
   tracking a movement of the user's left and right pupils for at least two seconds after the first flash;
   controlling the light source to emit a second flash of light in a left eye of the user;
   tracking a movement of the user's left and right pupils for at least two seconds after the second flash; and
   quantifying the level of impairment based upon the tracked movements of the user's left and right pupils.

5. The apparatus of claim 1, further comprising an external display coupled to an exterior of the housing, wherein the external display is operable to display a numeric score indicative of the quantified level of impairment.

6. The apparatus of claim 1, wherein the first and second cameras are operable to detect infrared light.

7. The apparatus of claim 1, wherein the light source comprises LEDs operable to emit light having a wavelength of about 420-490 nm.

8. The apparatus of claim 4, wherein the microcontroller tracking during the pupil reflex task includes the microcontroller:
   controlling the first camera to record a direction, a movement, and a pupillary response of a right pupil of the user for at least two seconds; and
   controlling the second camera to record a direction, a movement, and a pupillary response of a left pupil of the user for at least two seconds.

9. The apparatus of claim 8 wherein the pupillary response of the right and left pupils comprise a percent dilation or constriction, a time constant for dilation or constriction, a duration of dilation or constriction, or a rate of dilation or constriction.

10. The apparatus of claim 1 wherein the apparatus is configured to measure an orientation of a right pupil of the user and an orientation of a left pupil of the user.

11. A method of quantifying a level of neurological impairment after an acute neurological event, the method comprising:
   emitting a first flash of one of: blue, red, or white light, into only a user's left eye;
   tracking a movement of a user's left and right pupils for at least two seconds after the first flash;
   emitting a second flash of one of: blue, red, or white light, into only a user's right eye;
   tracking a movement of the user's left and right pupils for at least two seconds after the second flash;
   calculating an event numeric score based upon a combination of the tracked movements of the user's left and right pupils, wherein the tracked movements include: contraction amplitude, latency, contraction velocity, and dilation velocity, of both the left and right pupils in response to both the first flash and the second flash; and
   comparing the event numeric score to a baseline numeric score acquired for the user prior to the acute neurological event, wherein a change between the event numeric score and the baseline numeric score is indicative of the level of impairment caused by the acute neurological event.

12. The method of claim 11, wherein the first and second flashes have an intensity of up to about 200 foot candles and a duration of up to about 10 seconds.

13. The method of claim 11, wherein the movement of the user's left and right pupils are tracked for approximately three seconds, and wherein the tracked movements further include orientations of both the left and right pupils in response to both the first flash and the second flash.

14. The method of claim 11 wherein the movement of the user's left and right pupils are tracked using infrared light.

15. The method of claim 11, further comprising adapting a housing to fit over the user's right and left eyes and block external light from reaching the user's right and left eyes prior to emitting the first and second flashes.

16. A method of quantifying a level of neurological impairment, the method comprising:
    emitting a first flash of light into a user's eye;
    measuring a pupil diameter of the user's eye at a predetermined time after termination of the first flash;
    waiting until the pupil diameter of the user's eye returns to a steady state dark adaptation diameter after the first flash;
    emitting a second flash of light photopically matched with the first flash into the user's eye after the pupil diameter of the user's eye has returned to the steady state dark adaptation diameter;
    measuring the pupil diameter of the user's eye at the predetermined time after termination of the second flash, wherein the predetermined time is at least four seconds and is selected independent of the user's eye's reaction to either the first flash or the second flash; and
    calculating an isolated melanopsin response by comparing the pupil diameter measured at the predetermined time after termination of the second flash with the pupil diameter measured at the predetermined time after termination of the first flash, wherein one of the first flash or second flash is blue light and the other of the first flash or the second flash is one of: red or white light.

17. The method of claim 16, further comprising adapting a housing to fit over the user's eyes and block external light from reaching the user's eyes.

18. The method of claim 16, wherein the pupil diameters are measured at a time approximately six seconds after each of the first flash and the second flash.

19. The method of claim 16, wherein the other of the first flash or the second flash is red light.

20. The method of claim 11, wherein each of the emitting and tracking acts are repeated for each of the one of: blue, red, and white light, and wherein the method further comprises isolating a location of a disturbance to the pupil pathway using the tracked movements of the user's left and right pupils.

* * * * *